US012629291B2

(12) United States Patent     (10) Patent No.:   US 12,629,291 B2

Hesaka     (45) Date of Patent:     May 19, 2026

---

(54) WEARABLE ARTICLE PRODUCTION METHOD, WEARABLE ARTICLE, AND WEARABLE ARTICLE PRODUCTION DEVICE

(71) Applicant: ZUIKO CORPORATION, Osaka (JP)

(72) Inventor: Kazuyoshi Hesaka, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 854 days.

(21) Appl. No.: 17/603,420

(22) PCT Filed: Mar. 10, 2020

(86) PCT No.: PCT/JP2020/010359

§ 371 (c)(1),
(2) Date: Oct. 13, 2021

(87) PCT Pub. No.: WO2020/213299

PCT Pub. Date: Oct. 22, 2020

(65) Prior Publication Data

US 2022/0183902 A1     Jun. 16, 2022

(30) Foreign Application Priority Data

Apr. 15, 2019    (JP) ................................. 2019-076917

(51) Int. Cl.
   *A61F 13/15*      (2006.01)
   *A61F 13/49*      (2006.01)
          (Continued)

(52) U.S. Cl.
   CPC .... *A61F 13/15739* (2013.01); *A61F 13/4902* (2013.01); *B29C 65/08* (2013.01);
          (Continued)

(58) Field of Classification Search
   CPC ............ A61F 13/15739; A61F 13/4902; A61F 2013/15869; A61F 2013/49022;
          (Continued)

(56) References Cited

U.S. PATENT DOCUMENTS

2010/0051170 A1*   3/2010   Nakakado ......... A61F 13/15739
                                        156/73.1
2014/0130956 A1*   5/2014   Floberg ............. B29C 66/83411
                                        156/164

(Continued)

FOREIGN PATENT DOCUMENTS

CN      101652115     2/2010
CN      107205858     9/2017

(Continued)

OTHER PUBLICATIONS

International Search Report issued Jun. 16, 2020 in International (PCT) Application No. PCT/JP2020/010359.

(Continued)

*Primary Examiner* — Christopher W Raimund
(74) *Attorney, Agent, or Firm* — Wenderoth, Lind & Ponack, L.L.P.

(57)          ABSTRACT

A wearable article production method for a stretchable sheet having partially weakened stretchability includes a welding step of ultrasonically welding two sheet bodies and an elastic film to each other at plural joints separated from each other in a predetermined transport direction in a region including a predetermined attachment location by transporting a sheet laminate formed by sandwiching the elastic film in an elongated state between the two sheet bodies in the transport direction so that the sheet laminate passes between an anvil roll and an ultrasonic horn to form a stretchable sheet; a weakening step of forming weakened regions, where stretchability of the elastic film is weakened, at least at a part of the attachment location in the stretchable sheet after the (Continued)

welding step; and an attachment step of attaching an absorbent main body to the attachment location so that the absorbent main body overlaps the weakened regions.

6 Claims, 10 Drawing Sheets

(51) Int. Cl.
    *B29C 65/00*         (2006.01)
    *B29C 65/08*         (2006.01)
(52) U.S. Cl.
    CPC .... *B29C 66/21* (2013.01); *A61F 2013/15869* (2013.01); *A61F 2013/49022* (2013.01)
(58) Field of Classification Search
    CPC .......... A61F 13/15707; A61F 13/15804; A61F 13/49007; A61F 13/15699; B29C 65/08; B29C 66/21
    See application file for complete search history.

(56) References Cited

U.S. PATENT DOCUMENTS

| | | | |
|---|---|---|---|
| 2018/0008481 A1 | 1/2018 | Takahashi et al. | |
| 2018/0014984 A1 | 1/2018 | Sakai | |
| 2018/0147095 A1 | 5/2018 | Koshijima et al. | |
| 2018/0169964 A1* | 6/2018 | Schneider | A61F 13/15593 |
| 2020/0206038 A1* | 7/2020 | Bonelli | A61F 13/15731 |
| 2020/0297550 A1* | 9/2020 | Bäck | A61F 13/49011 |
| 2020/0383841 A1 | 12/2020 | Sakai | |
| 2020/0397623 A1 | 12/2020 | Takahashi et al. | |
| 2020/0397625 A1 | 12/2020 | Sakai | |
| 2020/0397626 A1 | 12/2020 | Sakai | |

FOREIGN PATENT DOCUMENTS

| | | | |
|---|---|---|---|
| CN | 107205859 | 9/2017 | |
| CN | 107847359 | 3/2018 | |
| CN | 107921772 | 4/2018 | |
| JP | 2008-148942 | 7/2008 | |
| JP | 5964477 | 8/2016 | |
| JP | 2016-185265 | 10/2016 | |
| JP | 2016-193199 | 11/2016 | |
| WO | 2017/002207 | 1/2017 | |
| WO | 2018/186318 | 10/2018 | |
| WO | WO-2018186318 A1 * | 10/2018 | A61F 13/15 |

OTHER PUBLICATIONS

Extended European Search Report issued May 13, 2022 in European Application No. 20791707.1.
Office Action issued Jun. 21, 2022 in Chinese Application No. 202080028943.9 (with partial English translation).

* cited by examiner

FIG. 7

WEARABLE ARTICLE PRODUCTION METHOD, WEARABLE ARTICLE, AND WEARABLE ARTICLE PRODUCTION DEVICE

TECHNICAL FIELD

The present invention relates to a wearable article production method, a wearable article, and a wearable article production device.

BACKGROUND ART

Commonly used wearable articles such as disposable diapers include an exterior body having a front part and a back part and an interior body configured to absorb water.

The exterior body is required to have stretchability to fit the body and be worn, but a portion, to which the interior body is fixed, of the exterior body is required to have partially suppressed stretchability, namely, weakened stretchability from the viewpoint of retentivity of the interior body.

With regard to this point, there is a structure in which the stretchability of the elastic film at the portion, to which the interior body is fixed, of the exterior body having a stretchable sheet, in which an elastic film is sandwiched between a pair of sheet bodies, is partially weakened as the absorbent article described in Patent Literature 1.

Specifically, in Patent Literature 1, a laminate, in which an elastic film in an elongated state is sandwiched between a pair of sheet bodies, is ultrasonically welded by an ultrasonic horn in a state of being wound around the surface of the anvil roll. In this ultrasonic welding, a plurality of point-like joints are formed on the laminate at the positions of a plurality of pressure convex portions formed on the surface of the anvil roll, and the laminates are joined to each other at the joints to form a stretchable sheet having a laminated structure. The portion, of which the stretchability is desired to be weakened, of the stretchable sheet is ultrasonically welded using a large number of pressure convex portions provided on the anvil roll at a high density so that the number of joints partially increases. This partially increases the area ratio of joints, namely, the proportion of the area occupied by joints per unit area, and the stretchability of the stretchable sheet is thus weakened.

However, in the case of producing the absorbent article described in Patent Literature 1, there is a problem that the temperature of the anvil roll, on which the stretchable sheet is wound, or the ultrasonic horn becomes too high by performing ultrasonic welding mainly in the range of a part using a large number of pressure convex portions provided on the anvil roll at a high density when a region having a high area ratio of joints is formed in the stretchable sheet. As a result, the portion other than the joints in the stretchable sheet also melts, and it is difficult to continuously process the stretchable sheet.

CITATION LIST

Patent Literature

Patent Literature 1: JP 2016-193199 A

SUMMARY OF INVENTION

The present invention has been made in view of the above circumstances, and an object thereof is to provide a wearable article production method, by which a stretchable sheet having partially weakened stretchability can be continuously processed, a wearable article, and a wearable article production device.

In order to solve the above problems, a wearable article production method of the present invention is a production method of a wearable article including a stretchable sheet having stretchability and an absorbent main body that is attached to a predetermined attachment location in the stretchable sheet and is configured to absorb water, the production method including: a welding step of ultrasonically welding a pair of sheet bodies and an elastic film to each other at a plurality of joints separated from each other in a predetermined transport direction in a region including the attachment location by transporting a sheet laminate formed by sandwiching the elastic film in an elongated state between the pair of sheet bodies in the transport direction so that the sheet laminate passes between an anvil roll and an ultrasonic horn to form the stretchable sheet; a weakening step of forming a weakened region, where stretchability of the elastic film is weakened, at least at a part of the attachment location in the stretchable sheet after the welding step; and an attachment step of attaching the absorbent main body to the attachment location so that the absorbent main body overlaps the weakened region.

A wearable article according to an aspect of the present invention includes a stretchable sheet having stretchability; and an absorbent main body configured to absorb water, in which the absorbent main body is attached to a predetermined attachment location in the stretchable sheet, the stretchable sheet includes an elastic film having stretchability in a predetermined stretching direction and a pair of sheet bodies, the elastic film and the pair of sheet bodies are ultrasonically welded to each other at a plurality of joints by the plurality of joints separated from each other in the stretching direction in a state in which the elastic film in an elongated state is sandwiched between the pair of sheet bodies, a weakened region, where stretchability of the elastic film is weakened, is formed at least at a part of the attachment location in the stretchable sheet by a plurality of notches, and the absorbent main body is attached to the attachment location so as to overlap the weakened region.

A wearable article production device of the present invention is a production device of a wearable article including a stretchable sheet having stretchability and an absorbent main body that is attached to a predetermined attachment location in the stretchable sheet and is configured to absorb water, which includes a welding unit for ultrasonically welding a pair of sheet bodies and an elastic film to each other at a plurality of joints separated from each other in a predetermined transport direction in a region including the attachment location by transporting a sheet laminate formed by sandwiching the elastic film in an elongated state between the pair of sheet bodies in the transport direction so that the sheet laminate passes between an anvil roll and an ultrasonic horn to form the stretchable sheet; a weakening unit that is arranged on a downstream side of the welding unit in the transport direction and is for forming a weakened region, where stretchability of the elastic film is weakened, at least at a part of the attachment location in the stretchable sheet; and an attachment unit that is arranged on a downstream side of the welding unit in the transport direction and is for attaching the absorbent main body to the attachment location so that the absorbent main body overlaps the weakened region.

BRIEF DESCRIPTION OF DRAWINGS

FIG. 7 is an enlarged front view illustrating a configuration of a vent hole forming unit including a second anvil roll and a perforated roll for vent hole formation in FIG. 5.

DESCRIPTION OF EMBODIMENTS

Hereinafter, preferred embodiments of the present invention will be described in detail with reference to the accompanying drawings.

First Embodiment

Figure 1:
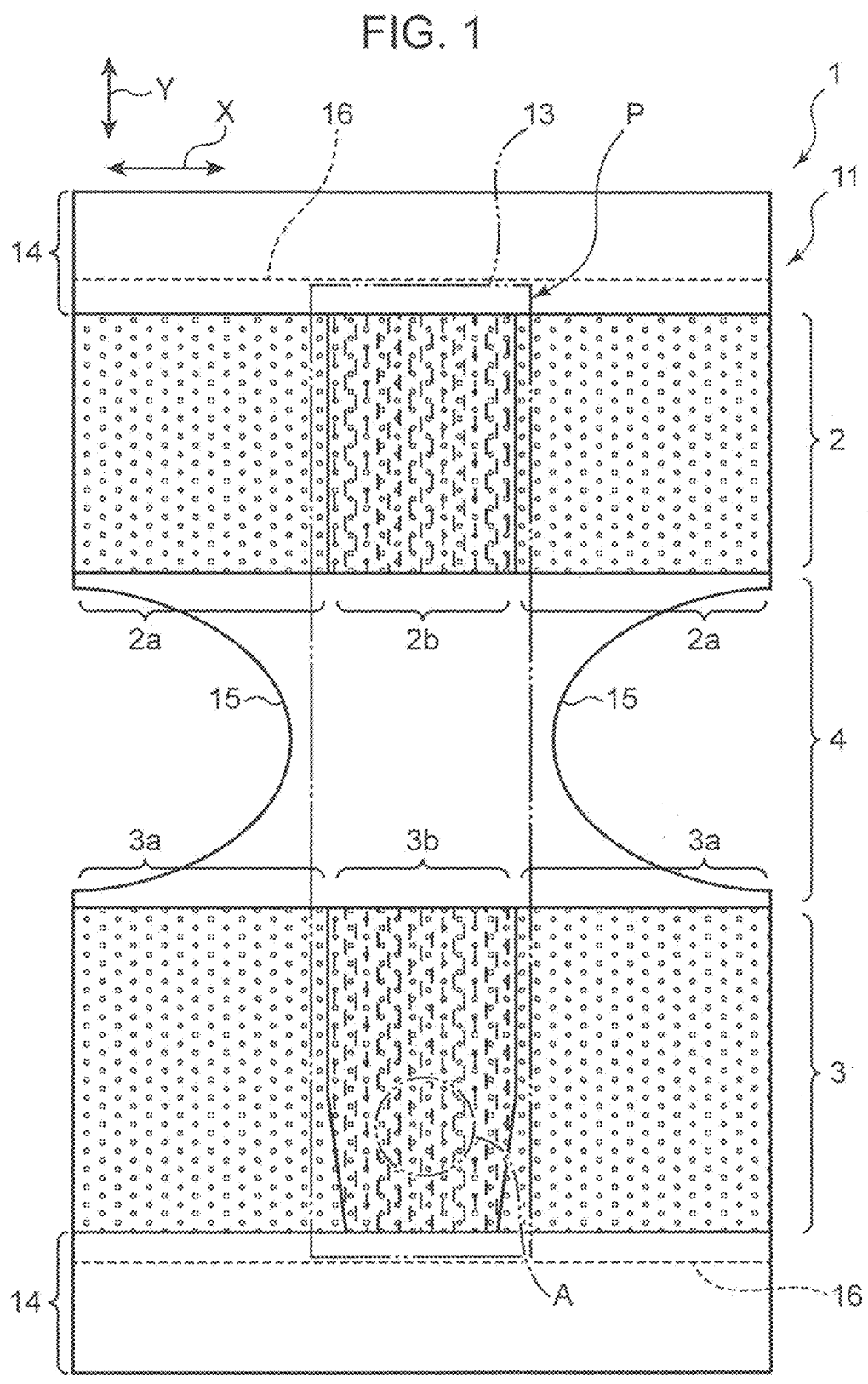
FIG. 1 is a plan view illustrating a state in which a wearable article according to a first embodiment of the present invention is unfolded.

As a first embodiment of the present invention, a wearable article 1 illustrated in FIG. 1 has a form in which a disposable diaper as an example is unfolded, but may have other forms.

The wearable article 1 illustrated in FIG. 1 mainly includes a stretchable sheet 11 having stretchability and an absorbent main body 13 configured to absorb water. The absorbent main body 13 is attached to a predetermined attachment location P in the stretchable sheet 11 (namely, the region extending in an orthogonal direction Y near the center of a stretching direction X of the stretchable sheet 11 in FIG. 1).

As illustrated in FIG. 1, the wearable article 1 having the form of a disposable diaper has a front abdomen 2 constituting a front part, a back abdomen 3 constituting a back part, and a crotch 4 constituting a crotch part in the unfolded state. The crotch 4 connects the front abdomen 2 and the back abdomen 3. The attachment location P of the absorbent main body 13 is set in a range continuing in the orthogonal direction Y including the central portion in the stretching direction X of each of these front abdomen 2, back abdomen 3, and crotch 4. A folding portion 14 is continuously provided at the upper end of the front abdomen 2 and the lower end of the back abdomen 3. A leg hole 15, which is a substantially semicircular hole into which a leg can be inserted, is formed at the crotch 4.

The front abdomen 2 has a stretching region 2a having stretchability that allows stretching in the stretching direction X around the waist on both the left and right sides and a weakened region 2b having weakened stretchability in the center, and these stretching region 2a on both the left and right sides and weakened region 2b in the center are continuously formed. Similar to the front abdomen 2, the back abdomen 3 also has a stretching region 3a having stretchability that allows stretching in the stretching direction X around the waist on both the left and right sides and a weakened region 3b having weakened stretchability in the center, and these stretching region 3a on both the left and right sides and weakened region 3b in the center are continuously formed. The front weakened region 2b and the rear weakened region 3b are formed at least at a part of the attachment location P in the stretchable sheet 11, and are formed at a part of the attachment location P in FIG. 1, but may be formed in a range covering the whole attachment location P.

Figure 3A:
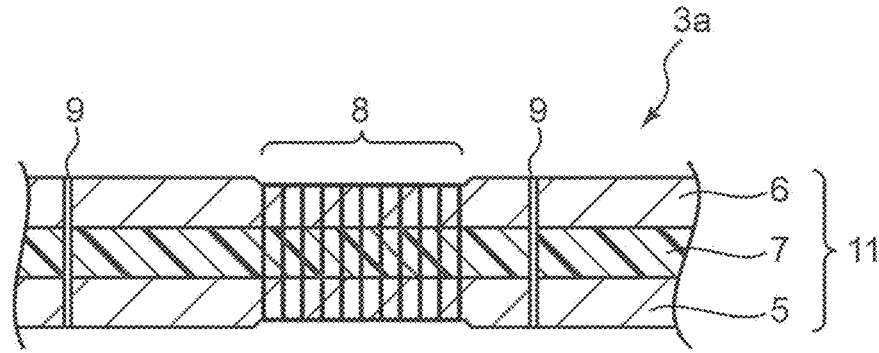
FIG. 3A is an enlarged sectional view of a stretching region in FIG. 1.
Figure 3B:
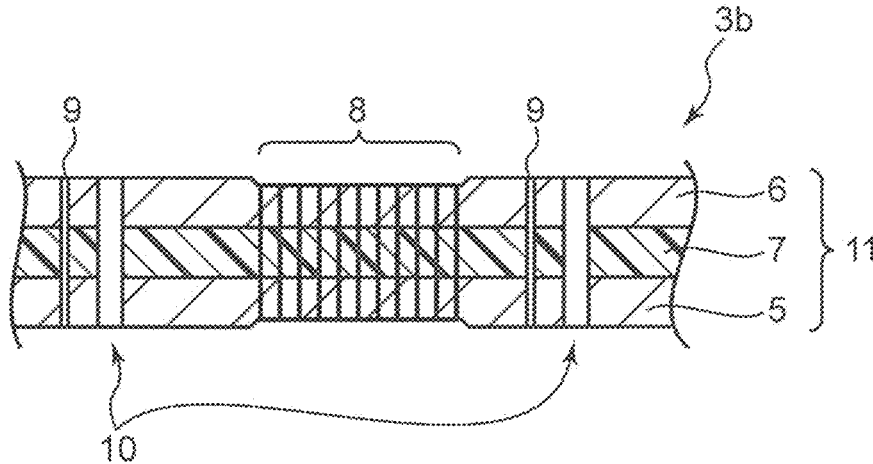
FIG. 3B is an enlarged sectional view of the weakened region in FIG. 1.

As illustrated in FIGS. 3A and 3B, the stretchable sheet 11 includes a pair of sheet bodies 5 and 6 and an elastic film 7 having stretchability. The stretchable sheet 11 is formed by sandwiching the elastic film 7 between the pair of sheet bodies 5 and 6 from both the front and back surfaces in the whole range of the front abdomen 2 and back abdomen 3 in FIG. 1 (namely, the whole range of stretching regions 2a and 3a and weakened regions 2b and 3b) and ultrasonically welding these to each other. In other words, the elastic film 7 and the pair of sheet bodies 5 and 6 are ultrasonically welded to each other at a plurality of joints 8 that are separated from each other in the stretching direction X and the orthogonal direction Y orthogonal to the stretching direction X in a state in which the elastic film 7 in an elongated state in the stretching direction X is sandwiched between the pair of sheet bodies 5 and 6.

Portions other than the front abdomen 2 and back abdomen 3 of the stretchable sheet 11 in FIG. 1, for example, the crotch 4 and the folding portion 14 are formed of one sheet body 5 of the pair of sheet bodies 5 and 6 (sheet body on the outer side of the wearable article 1 in the form of disposable diaper).

Figure 2:
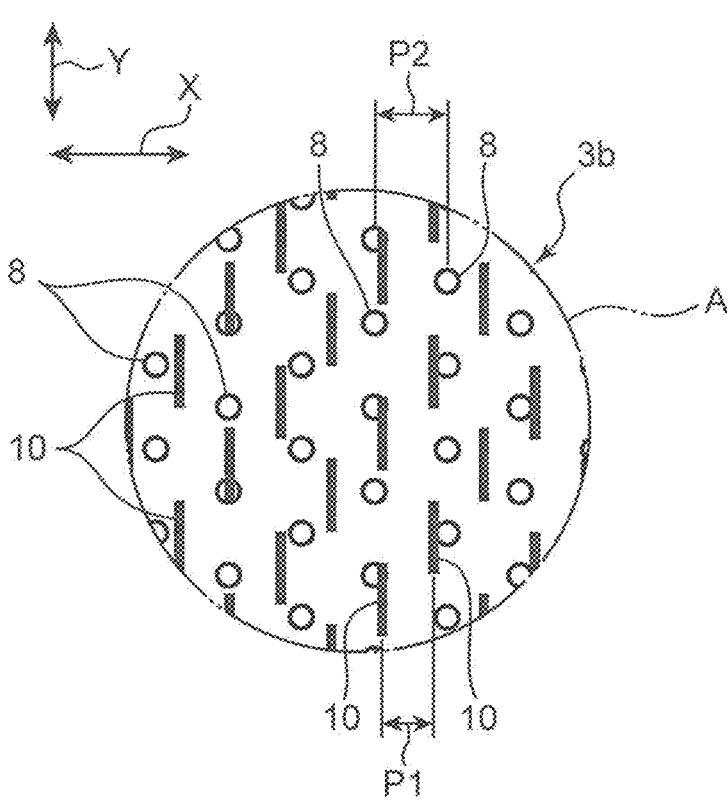
FIG. 2 is an enlarged plan view of a portion A of the weakened region in FIG. 1.

As the weakened region 3b of the back abdomen 3 illustrated in FIGS. 2 and 3B, in the first embodiment, the weakened region 3b where the stretchability of the elastic film 7 is weakened is formed at least at a part of the attachment location P of the stretchable sheet 11 by a plurality of notches 10 formed to be separated from each other in the stretching direction X and the orthogonal direction Y. Although not illustrated, the weakened region 2b of the front abdomen 2 is also formed by weakening the stretchability of the elastic film 7 by the plurality of notches 10 in the same manner as the weakened region 3b described above.

As illustrated in FIG. 2, in the orthogonal direction Y orthogonal to the stretching direction X, an arrangement pitch P1 in the stretching direction X of the row formed by the notches 10 (namely, the column in FIG. 2) is smaller than an arrangement pitch P2 in the row formed by the joints 8 (the column in FIG. 2).

The plurality of notches 10 illustrated in FIG. 2 are arranged so that three rows of notches 10 adjacent to each other when viewed in the stretching direction X are continuous in the orthogonal direction Y.

The length of the notch 10 is not particularly limited in the present invention, but it is preferable that the length of the notch 10 is larger than the diameter of the joint 8 since the effect of weakening the elastic film 7 by the notch 10 is reliably obtained. For example, when the diameter of the joint 8 is about 1 mm, the length of the notch 10 is set in the range of several mm to 10 mm.

The absorbent main body 13 is attached to the attachment location P by heat sealing, bonding using an adhesive material, or the like so as to overlap the weakened regions 2b and 3b in the stretchable sheet 11 as illustrated in FIG. 1.

The stretchable sheet 11 is processed into the form of a disposable diaper as the folding portion 14 is folded back along a folded line 16 into the front abdomen 2 and the back abdomen 3 in a state in which the absorbent main body 13 is attached to the attachment location P, the approximately semicircular leg holes 15 into which legs can be inserted are formed at positions on both sides of the absorbent main body 13, these side portions are sealed (so-called side sealing) in a state in which the front abdomen 2 and the back abdomen 3 overlap each other, and the adjacent stretchable sheets 11 are cut from each other.

The sheet bodies 5 and 6 are not particularly limited in the present invention as long as they are in the form of a sheet having flexibility, but are preferably a sheet material having breathability and flexibility considering that the sheet bodies 5 and 6 are used in wearable articles such as disposable diapers. As the sheet material having breathability and flexibility, for example, a non-woven fabric and the like are adopted. A non-woven fabric is produced using a synthetic fiber such as an olefin-based fiber such as polypropylene or polyethylene, a polyester-based fiber, or a polyamide-based fiber.

The elastic film 7 is only required to be a film-like material having higher elasticity (in other words, stretchability) than the sheet bodies 5 and 6, and for example, a resin film formed of a thermoplastic elastomer is used as the elastic film 7. The thermoplastic elastomer is selected from, for example, at least one of a styrene-based elastomer, an olefin-based elastomer, a polyester-based elastomer, a polyamide-based elastomer, or a urethane elastomer.

Figure 4:
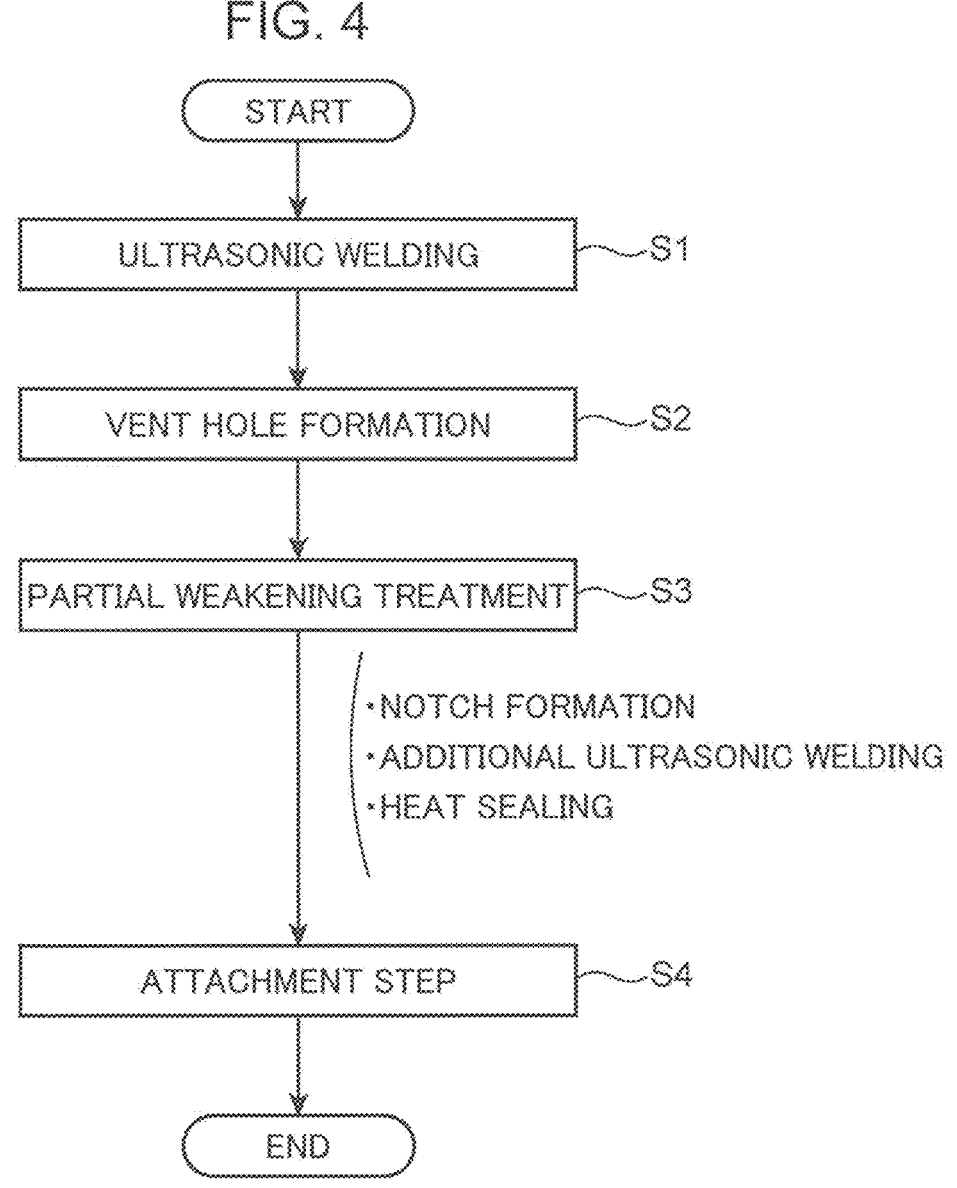
FIG. 4 is a flowchart illustrating a wearable article production method according to an embodiment of the present invention.

When the wearable article 1 configured as described above is produced, the wearable article 1 is produced according to steps illustrated in the flowchart of FIG. 4.

First, a welding step by ultrasonic welding is performed in order to form the stretchable sheet 11 in step S1. Specifically, in a wearable article production device 21 illustrated in FIG. 5, the elastic film 7 is transported while being sandwiched between a first anvil roll 22 and a pressing roll 23. At this time, the elastic film 7 is transported in a state of being elongated in the transport direction. The elastic film 7 in an elongated state is then sandwiched between the pair of sheet bodies 5 and 6 to form a sheet laminate. Hence, when the stretchable sheet 11 in FIG. 1 is viewed, the stretchable sheet 11 is transported in a predetermined transport direction (stretching direction in FIG. 1) so that the stretching direction X and the transport direction coincide with each other.

At this time, the elastic film 7 and the upper sheet body 6 are branched into two and transported in advance so as to correspond to the front abdomen 2 and the back abdomen 3 in FIG. 1 before the sheet laminate is formed, and are superposed on the lower sheet body 5 extending over the whole range of the stretchable sheet 11 in FIG. 1 to form a sheet laminate.

Figure 5:
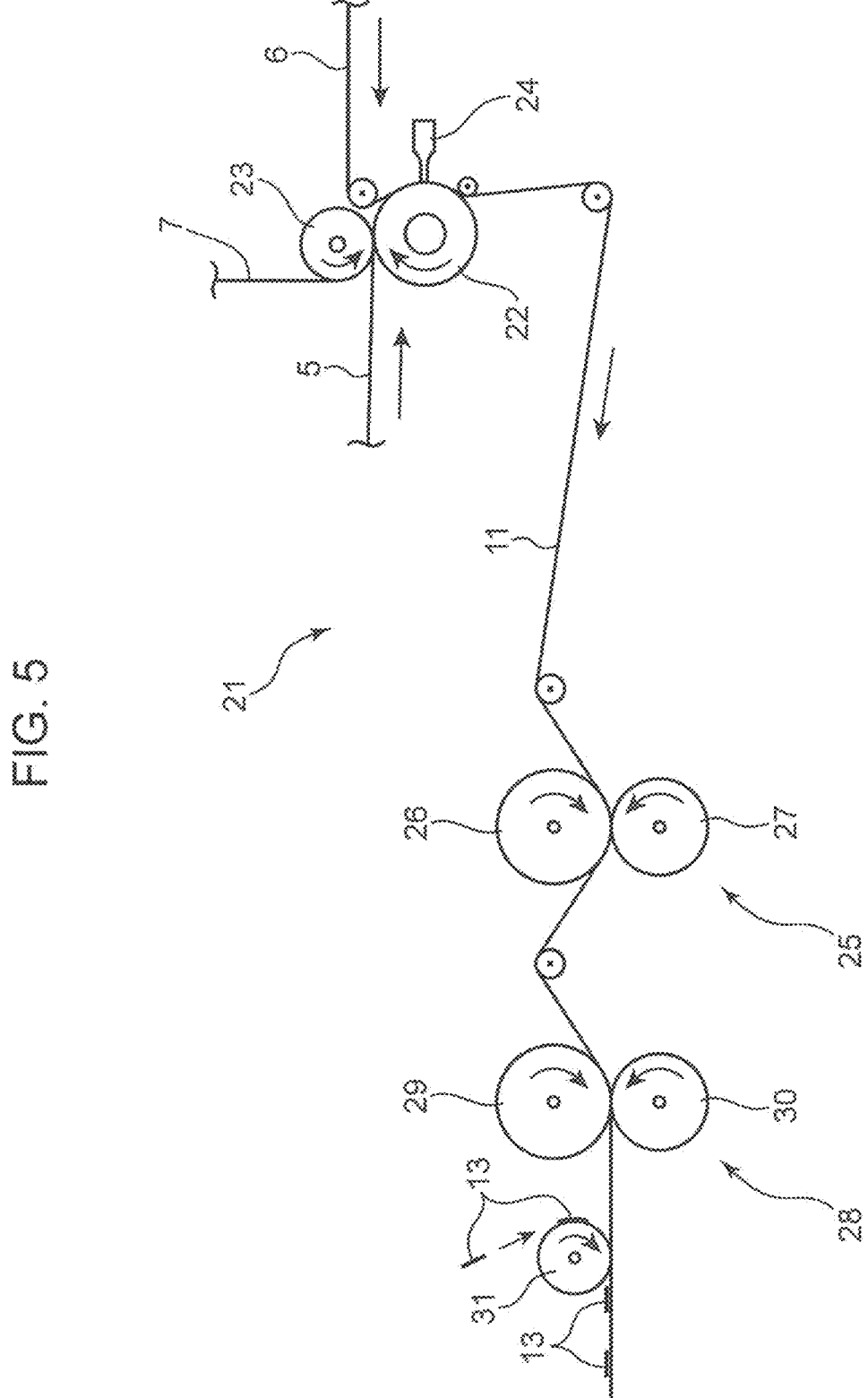
FIG. 5 is a diagram schematically illustrating a configuration of a wearable article production device according to an embodiment of the present invention used in a series of production method illustrated in FIG. 4.
Figure 6:
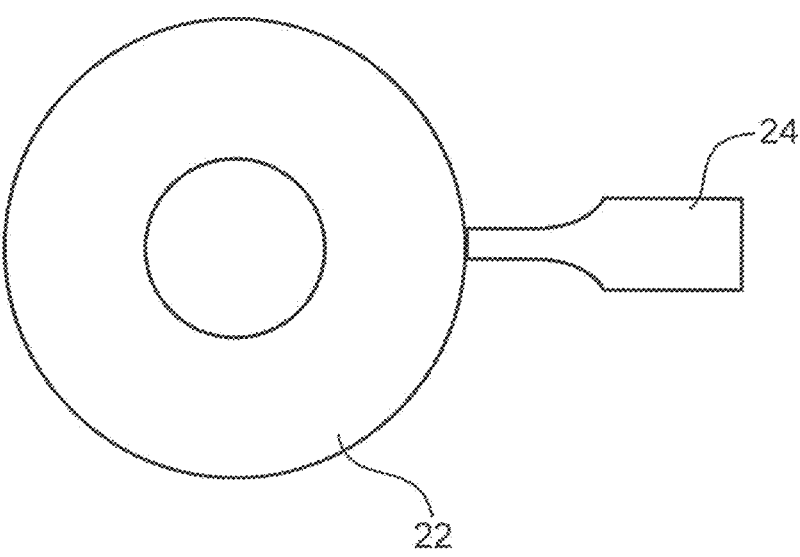
FIG. 6 is an enlarged front view illustrating a configuration of the first anvil roll and the ultrasonic horn for ultrasonic welding in FIG. 5.

The sheet laminate is then transported so as to pass between the first anvil roll 22 and an ultrasonic horn 24 that are illustrated in FIGS. 5 and 6, and the pair of sheet bodies 5 and 6 and the elastic film 7 are ultrasonically welded to each other at a plurality of joints 8 (see FIGS. 2 and 3), which are separated from each other in the transport direction (stretching direction X) and the orthogonal direction Y orthogonal to the transport direction in a region including the attachment location P of the absorbent main body 13 to form the stretchable sheet 11. In the production device 21 of the present embodiment, welding unit is formed of the first anvil roll 22 and the ultrasonic horn 24.

By this ultrasonic welding, a large number of joints 8 are formed over the region including the attachment location P of the absorbent main body 13 as illustrated in FIGS. 1 to 3, specifically over a portion at which the pair of sheet bodies 5 and 6 and the elastic film 7 are laminated, namely, the whole range of the front abdomen 2 and back abdomen 3 illustrated in FIG. 1.

Figure 7:
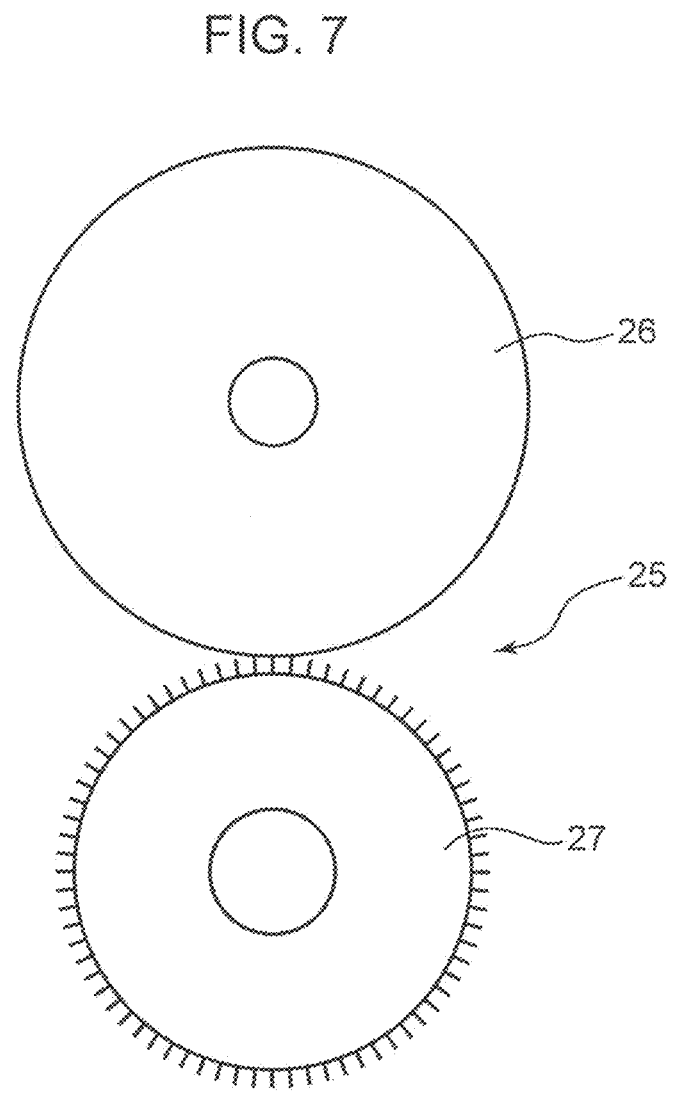

After the ultrasonic welding step (S1), a vent hole forming step of forming a vent hole 9 (see FIG. 3) in the elastic film 7 is performed in step S2. Specifically, as illustrated in FIGS. 5 and 7, the stretchable sheet 11 is sent to a piercing unit 25. The piercing unit 25 includes a second anvil roll 26 and a piercing roll 27 in which a large number of pins arranged so as to face the second anvil roll 26 are formed on the peripheral surface of the roll. By allowing the stretchable sheet 11 to pass between the second anvil roll 26 and the piercing roll 27, vent holes 9 (see FIG. 3) are uniformly formed in the whole region of the front abdomen 2 and back abdomen 3 of the stretchable sheet 11, namely, the stretching regions 2a and 3a and the weakened regions 2b and 3b.

By piercing the stretchable sheet 11 in a state in which the pins of the piercing roll 27 are heated, the elastic film 7 of the stretchable sheet 11 is thermoset in the opened state, and it is thus possible to maintain the vent holes 9 having a predetermined opening width. Since the sheet bodies 5 and 6 are formed of a material such as a non-woven fabric having breathability, the breathability is secured even when the opening is closed after piercing.

The diameter of the vent holes 9 is set to a minute size that allows gas (water vapor) to pass through but does not allow liquid (water, urine and the like) to pass through, and is set to be smaller than the diameter of the joint 8 (for example, about 1 mm). For example, the diameter of the vent holes 9 is set to 0.1 to 0.8 mm, and the density of the vent holes 9 is set to 15 to 100 holes/cm². The diameter of the vent holes 9 is set based on the diameter of the pin that presses the stretchable sheet 11 (namely, the elastic film 7 on the inside of the stretchable sheet 11) in the elongated state.

After the ultrasonic welding step (S1) and vent hole forming step (S2) described above, a weakening step of performing a partial weakening treatment as in step S3 is performed. Specifically, weakened regions 2b and 3b where the stretchability of the elastic film 7 is weakened are formed at least at a part of the attachment location P of the stretchable sheet 11. The notch 10 is formed in the weakening step of the first embodiment, but additional ultrasonic welding, heat sealing and the like are performed in the second and third embodiments described later.

In other words, in the weakening step of step S3 in the first embodiment, as illustrated in FIGS. 2 and 3B, the weakened regions 2b and 3b are formed at least at a part of the attachment location P by forming the plurality of notches 10 to be separated from each other in the stretching direction X and the orthogonal direction Y in the stretchable sheet 11.

Figure 8:
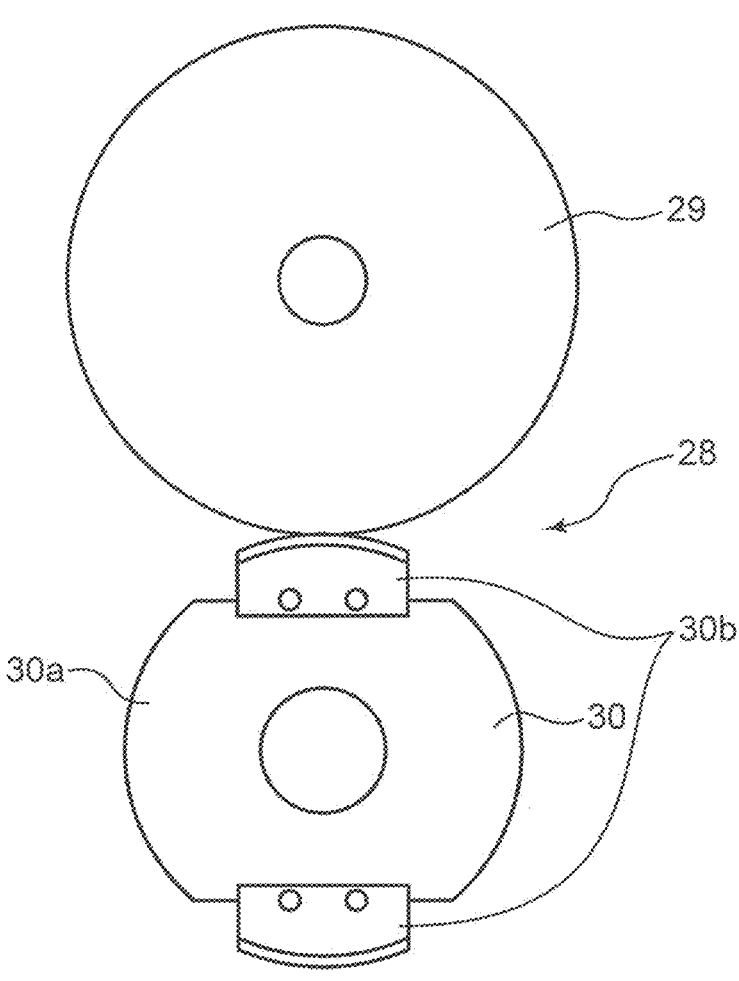
FIG. 8 is an enlarged front view illustrating a configuration of a notch forming unit including a third anvil roll and a rotary cutter in FIG. 5.

More specifically, in the weakening step, the plurality of notches 10 are formed at least at a part of the attachment location P using a notch forming unit 28 illustrated in FIGS. 5 and 8 while continuously transporting the stretchable sheet 11. Specifically, the notch forming unit 28 includes a third anvil roll 29 and a cutter roll 30 having a plurality of cutters 30b provided on the peripheral surface of 30a. Although not illustrated, a plurality of cutting protrusions facing the plurality of cutters 30b of the cutter roll 30 are formed on the peripheral surface of the third anvil roll 29.

By allowing the stretchable sheet 11 to pass between the third anvil roll 29 and the cutter roll 30, the plurality of notches 10 are formed at least at a part of the attachment location P so as to be separated from each other in the stretching direction X and the orthogonal direction Y using the cutter roll 30 having the plurality of cutters 30b. The arrangement of the plurality of notches 10 is not particularly limited as long as the plurality of notches 10 are separated from each other.

At this time, in the weakening step, it is preferable to form the plurality of notches 10 in a state in which the cutter 30b is heated to a temperature higher than the melting point of the elastic film 7 (for example, about 120° C. to 140° C.). By this, the notches 10 are not blocked even in a state in which the elastic film 7 is contracted.

In the production device 21 of the present embodiment, the weakening unit is configured by the notch forming unit 28 including the third anvil roll 29 and the cutter roll 30.

Subsequently, an attachment step of the absorbent main body 13 in step S4 is performed. Specifically, the absorbent main body 13 is attached to the attachment location P so as to overlap the weakened regions 2b and 3b of the stretchable sheet 11 by heat sealing, bonding using an adhesive material, or the like. With regard to the attachment of the absorbent main body 13, the absorbent main body 13 can be attached to the predetermined attachment location P of the stretchable sheet 11 at a predetermined interval by, for example, attaching the absorbent main body 13 to the peripheral surface of a transfer roll 31 and allowing the stretchable sheet 11 to pass under the transfer roll 31. In the production device 21 of the present embodiment, the attachment unit is configured by the transfer roll 31.

Finally, the stretchable sheet 11 is processed into a predetermined form, for example, the form of a disposable diaper, and the production of the wearable article 1 is thus completed. Specifically, the stretchable sheet 11 illustrated in FIG. 1 is processed into the form of a disposable diaper as leg holes 15 into which legs can be inserted are formed at positions on both sides of the absorbent main body 13 in a state in which the absorbent main body 13 is attached to the attachment location P, these side portions are sealed (so-called side sealing) in a state in which the front abdomen 2 and the back abdomen 3 overlap each other, and the adjacent stretchable sheets 11 are cut from each other as described above.

Features of First Embodiment (1)

The production method of the wearable article 1 of the first embodiment includes, after the welding step by ultrasonic welding of forming the stretchable sheet 11 by ultrasonic welding in the region including the attachment location P, a weakening step of weakening the stretchability of the elastic film 7 at least at a part of the attachment location P for the absorbent main body 13 in the stretchable sheet 11 as a step different from the welding step. By this, ultrasonic welding is not mainly performed in the range of a part in order to form the weakened regions 2b and 3b when the stretchable sheet 11 is formed and the temperature of the first anvil roll 22 or the ultrasonic horn 24 does not rise as in the conventional case. As a result, the portion other than the joints 8 in the stretchable sheet 11 does not melt, and the stretchable sheet 11 having partially weakened stretchability can be continuously processed.

(2)

In the production method of the wearable article 1 of the first embodiment, in the weakening step of S3, the weakened regions 2b and 3b are formed at least at a part of the attachment location P by forming the plurality of notches 10 to be separated from each other in the stretching direction X and the orthogonal direction Y in the stretchable sheet 11. This makes it possible to easily and reliably weaken the stretchability of the elastic film 7 and to form the weakened regions 2b and 3b in a predetermined range.

(3)

In the production method of the wearable article 1 of the first embodiment, the plurality of notches 10 are formed at least at a part of the attachment location P using the cutter roll 30 having a plurality of cutters 30b provided on the peripheral surface of 30a while continuously transporting the stretchable sheet 11 in the weakening step. In this way, it is possible to continuously form the plurality of notches 10 at the attachment location P in the stretchable sheet 11 that is continuously transported by using the cutter roll 30, and the processing efficiency in the weakening step is improved.

(4)

In the production method of the wearable article 1 of the first embodiment, the plurality of notches 10 are formed in a state in which the cutter 30b is heated to a temperature higher than the melting point of the elastic film 7 (for example, about 120° C. to 140° C.) in the weakening step. This makes it possible to more easily form the notches 10 in the elastic film 7.

(5)

The production method of the wearable article 1 of the first embodiment includes a vent hole forming step of forming the vent holes 9 in the elastic film 7 after the welding step. This makes it possible to impart breathability to the elastic film 7.

(6)

In the wearable article 1 of the first embodiment, the stretchable sheet 11 includes the elastic film 7 having stretchability and the pair of sheet bodies 5 and 6, and the elastic film 7 and the pair of sheet bodies 5 and 6 are ultrasonically welded to each other at the plurality of joints 8 in a state in which the elastic film 7 in the elongated state is sandwiched between the pair of sheet bodies 5 and 6. The weakened regions 2b and 3b where the stretchability of the elastic film 7 is weakened are formed at least at a part of the attachment location P, to which the absorbent main body 13 is attached, in the stretchable sheet 11 by the plurality of notches 10 formed in the stretchable sheet 11. By this, ultrasonic welding is not mainly performed in the range of a part when the stretchable sheet 11 is formed and the temperature of the first anvil roll 22 or the ultrasonic horn 24 does not rise as in the conventional case. As a result, the portion other than the joints 8 in the stretchable sheet 11 does not melt, and the stretchable sheet 11 having partially weakened stretchability can be continuously processed. Moreover, the weakened regions 2b and 3b are formed by the plurality of notches 10, and it is thus possible to easily and reliably weaken the stretchability of the elastic film 7 and to form the weakened regions 2b and 3b in a predetermined range.

(7)

In the wearable article production device 21 of the first embodiment, it is possible to form the stretchable sheet 11 by ultrasonic welding in the region including the attachment location P in the welding unit (welding unit including the first anvil roll 22 and the ultrasonic horn 24), and then weaken the stretchability of the elastic film 7 at least at a part of the attachment location P for the absorbent main body 13 in the stretchable sheet 11 in the weakening unit (the notch forming unit 28 including the third anvil roll 29 and the cutter roll 30) arranged on the downstream side of the welding unit in the transport direction. By this, ultrasonic welding is not mainly performed in the range of a part in order to form the weakened regions when the stretchable sheet 11 is formed and the temperature of the anvil roll or the ultrasonic horn does not rise as in the conventional case. As a result, the portion other than the joints in the stretchable sheet 11 does not melt, and the stretchable sheet 11 having partially weakened stretchability can be continuously processed.

Second Embodiment

In the first embodiment, as a weakening step of forming the weakened regions 2b and 3b, where the stretchability of the elastic film 7 is weakened, at least at a part of the attachment location P of the stretchable sheet 11, the notches 10 are formed, but the present invention is not limited to this, and another weakening step may be adopted as long as it is possible to form the weakened regions 2b and 3b where the stretchability of the elastic film 7 is weakened.

In other words, in the production method of a wearable article 1 according to a second embodiment of the present invention, the weakened regions 2b and 3b are formed at least at a part of the attachment location P by additionally performing ultrasonic welding on the stretchable sheet 11 to form additional joints 8 as the weakening step.

Figure 9A:
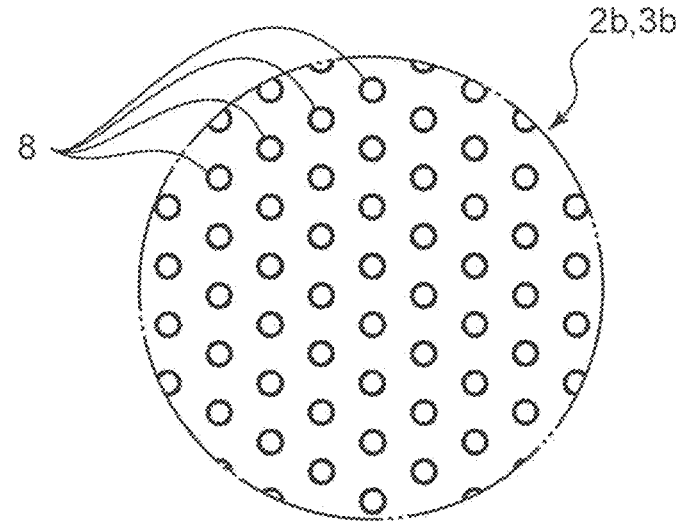
FIG. 9A is an enlarged plan view of a weakened region in a wearable article according to a second embodiment of the present invention.
Figure 9B:
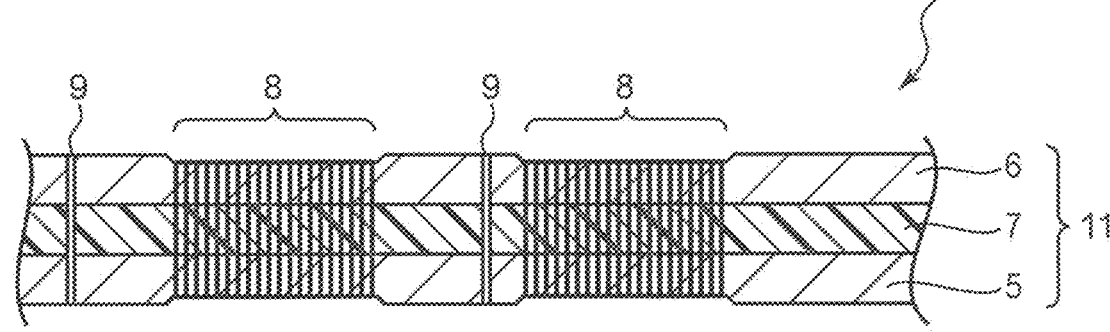
FIG. 9B is an enlarged sectional view of the weakened region in FIG. 9A.

In other words, in the weakening step of the second embodiment, as illustrated in FIGS. 9A and 9B, it is possible to form the weakened regions 2b and 3b at a density higher than the density of the joints 8 of the stretching regions 2a and 3a (see FIGS. 2 and 3B) by forming additional joints 8 instead of forming the notches 10 of the first embodiment (see FIGS. 2 and 3B).

In order to perform the weakening step of the second embodiment, in the production device 21 of the wearable article 1 illustrated in FIG. 5, an ultrasonic welding unit including an additional anvil roll and an additional ultrasonic horn may be installed instead of the notch forming unit 28.

In the case of forming the additional joints 8 in the weakening step, the additional joints 8 may be formed by changing the phase (namely, the arrangement pattern) and the size from those of the plurality of joints 8 formed during the welding step.

In other words, in the case of performing the weakening treatment to form the additional joints 8 by ultrasonic welding, the weakening treatment may be performed at least in a region other than the plurality of joints 8 formed during the welding step.

Since the steps other than the weakening step in the production method of the second embodiment are common to those in the production method of the first embodiment, the description thereof will be omitted.

In the production method of the wearable article 1 according to the second embodiment, it is possible to locally increase the number of joints 8 and to form the weakened regions 2b and 3b at least at a part of the attachment location P by additionally performing ultrasonic welding on the stretchable sheet 11 to form additional joints 8 as a weakening step after the welding step. In this production method as well, ultrasonic welding (for example, ultrasonic welding by the ultrasonic horn 24 in FIG. 5) is not simultaneously and mainly performed in the range of a part in the welding step when the stretchable sheet 11 is formed and the temperature of the first anvil roll 22 or the ultrasonic horn 24 does not rise as in the conventional case. As a result, the portion other than the joints 8 in the stretchable sheet 11 does not melt, and the stretchable sheet 11 having partially weakened stretchability can be continuously processed. Moreover, in this weakening step, it is possible to form additional joints 8 in an arbitrary number and arbitrary arrangement by additional ultrasonic welding, and thus the degree of freedom in formation of the weakened regions 2b and 3b is high.

Third Embodiment

As a third embodiment of the present invention, heat sealing may be performed as a weakening step after the welding step.

In other words, in the production method of a wearable article 1 according to the third embodiment of the present invention, as a weakening step, the weakened regions 2b and 3b are formed at a portion of at least a part of the attachment location P by bringing the portion into contact with a heated member (an embossing roll for heat embossing described later, or the like) to perform a heat-sealing of the pair of sheet bodies 5 and 6 and the elastic film 7 with each other.

More specifically, in the weakening step of the third embodiment, heat embossing is performed to form a predetermined shape by partially pressing the stretchable sheet 11 in the thickness direction of the stretchable sheet 11 while heating the stretchable sheet 11 as a specific example of heat sealing.

Figure 10A:
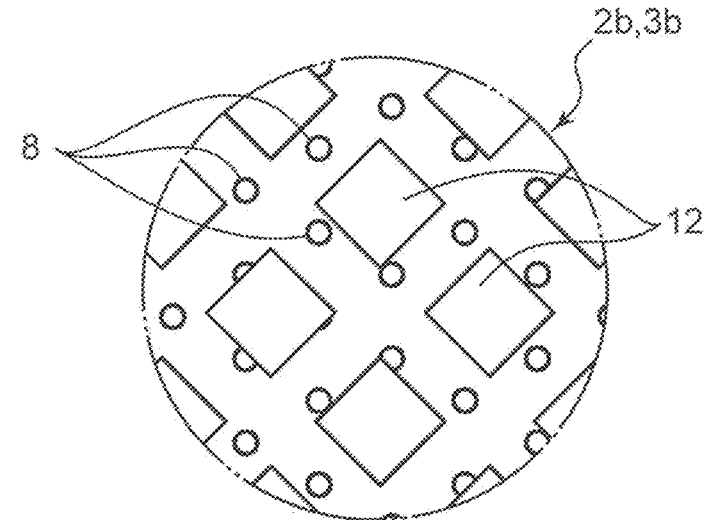
FIG. 10A is an enlarged plan view of a weakened region in a wearable article according to a third embodiment of the present invention.
Figure 10B:
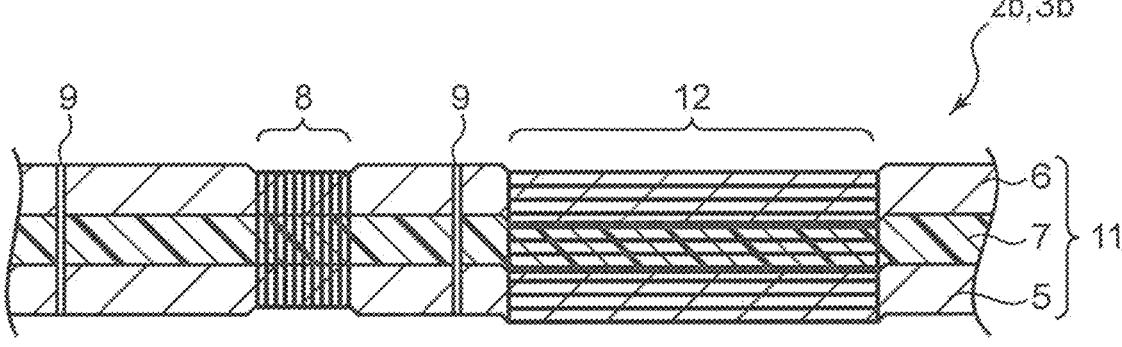
FIG. 10B is an enlarged sectional view of the weakened region in FIG. 10A.

In other words, in the weakening step of the third embodiment, as illustrated in FIGS. 10A and 10B, it is possible to form the weakened regions 2b and 3b, where the stretchability of the elastic film 7 is weakened, at least at a part of the attachment location P of the stretchable sheet 11 by forming a heat embossed portion 12 by heat embossing instead of forming the notches 10 of the first embodiment (see FIGS. 2 and 3B).

The shape and arrangement of the heat embossed portion 12 are not particularly limited in the present invention, and may be a desired pattern. For example, as the heat embossed portion 12 illustrated in FIG. 10A, a mosaic pattern or a tile pattern in which a large number of desired patterns are arranged may be formed in addition to a continuous pattern in which a large number of squares are arranged at intervals in the vertical and horizontal directions (a check pattern such as a so-called Japanese checkerboard pattern).

In other words, when the weakening treatment by heat sealing, specifically, the weakening treatment to form the heat embossed portion 12 by heat embossing is performed, the weakening treatment may be performed at least in a region other than the joints 8.

In order to perform heat embossing as a weakening step of the third embodiment, in the production device 21 of the wearable article 1 illustrated in FIG. 5, a heat embossing unit including a pair of embossing rolls, in which a plurality of convex portions (square convex portions in the case of a check pattern or a checkerboard pattern,) for forming the heat embossed portion 12 of a predetermined pattern are formed on the peripheral surface of the roll, and a heating unit for heating these embossing rolls may be installed instead of the notch forming unit 28.

When the heating temperature of the embossing rolls in the heat embossing is set, for example, to be higher than the melting point of the elastic film 7 (for example, about 120° C. to 140° C.) and to be lower than the melting point of the pair of sheet bodies 5 and 6 (for example, about 160° C.), the pair of sheet bodies 5 and 6 can be reliably heat-sealed to the elastic film 7 in a state in which the sheet bodies 5 and 6 do not peel off from the elastic film 7 and the sheet bodies 5 and 6 themselves do not melt.

In the third embodiment, the weakened regions 2*b* and 3*b* can be formed by performing heat sealing, in which the stretchable sheet is not pressed, other than the heat embossing in which the stretchable sheet is pressed while being heated.

Since the steps other than the weakening step in the production method of the third embodiment are common to those in the production method of the first embodiment, the description thereof will be omitted.

Features of Third Embodiment (1)

As described above, in the production method of the wearable article 1 of the third embodiment, the weakened regions 2*b* and 3*b* are formed at least at a part of the attachment location P by heat-sealing the pair of sheet bodies 5 and 6 and the elastic film 7 with each other in the weakening step.

In the wearable article 1 produced by the production method of the third embodiment, the weakened regions 2*b* and 3*b*, where the stretchability of the elastic film 7 is weakened, are formed at least at a part of the attachment location P of the stretchable sheet 11 by the portions at which the pair of sheet bodies 5 and 6 and the elastic film 7 are heat-sealed with each other. Since configurations other than this are the same as the configurations of the wearable article of the first embodiment, the description thereof will be omitted.

As described above, in the production method and the wearable article 1 produced by the production method of the third embodiment, ultrasonic welding is not mainly performed in the range of a part when the stretchable sheet 11 is formed and the temperature of the first anvil roll 22 or the ultrasonic horn 24 does not rise as in the conventional case. As a result, the portion other than the joints 8 in the stretchable sheet 11 does not melt, and the stretchable sheet 11 having partially weakened stretchability can be continuously processed. Moreover, in this weakening step, the weakened regions 2*b* and 3*b* are formed by heat-sealing the pair of sheet bodies 5 and 6 and the elastic film 7 with each other, and it is thus possible to arbitrarily change the state of bonding between the pair of sheet bodies 5, 6 and the elastic film 7 by changing the temperature for heat sealing. By setting the heat-sealed region as appropriate, it is possible to form a desired pattern (for example, a desired character or pattern) in the weakened regions 2*b* and 3*b*, and the design is improved.

(2)

In the production method of the wearable article 1 of the third embodiment, heat embossing is performed to form a predetermined shape by partially pressing the stretchable sheet 11 in the thickness direction of the stretchable sheet 11 while heating the stretchable sheet 11 as heat sealing.

In the wearable article 1 produced by the production method of the third embodiment, the stretchable sheet 11 is partially pressed in the thickness direction of the stretchable sheet 11 at the portion heat-sealed by heat embossing to form a predetermined shape.

In the production method and the wearable article 1 of the third embodiment, in which the heat embossing as described above is used, it is possible to reliably bond the pair of sheet bodies 5, 6 and the elastic film 7 to each other. Moreover, it is possible to realize a three-dimensional effect by imparting irregularity to the weakened regions 2*b* and 3*b* in a desired pattern, and the visibility is improved while the design is further improved.

Other Embodiments

In the first to third embodiments, the form of a pants-type disposable diaper as an example of the wearable article 1 has been described as an example, but the present invention is not limited to this, and can be applied to various forms of wearable articles as long as they include a stretchable sheet and an absorbent main body and the absorbent main body is attached to the weakened region that is formed in the stretchable sheet and has weakened stretchability. Hence, the wearable article and the production method thereof of the present invention can also be applied to various forms of disposable diapers such as tape type and pad type and further to sanitary napkins and the like in addition to pants-type disposable diapers.

Summary of Embodiments

The embodiments are summarized below.

The wearable article production method according to the embodiments is a production method of a wearable article including a stretchable sheet having stretchability and an absorbent main body that is attached to a predetermined attachment location in the stretchable sheet and is configured to absorb water, the production method including a welding step of ultrasonically welding a pair of sheet bodies and an elastic film to each other at a plurality of joints separated from each other in a predetermined transport direction in a region including the attachment location by transporting a sheet laminate formed by sandwiching the elastic film in an elongated state between the pair of sheet bodies in the transport direction so that the sheet laminate passes between an anvil roll and an ultrasonic horn to form the stretchable sheet; a weakening step of forming a weakened region, where stretchability of the elastic film is weakened, at least at a part of the attachment location in the stretchable sheet after the welding step; and an attachment step of attaching the absorbent main body to the attachment location so that the absorbent main body overlaps the weakened region.

The production method includes, after the welding step of forming a stretchable sheet by ultrasonic welding in the region including the attachment location, a weakening step of weakening the stretchability of the elastic film at least at a part of the attachment location for the absorbent main body in the stretchable sheet as a step different from the welding step. By this, ultrasonic welding is not mainly performed in the range of a part in order to form the weakened region when the stretchable sheet is formed and the temperature of the anvil roll or the ultrasonic horn does not rise as in the conventional case. As a result, the portion other than the joints in the stretchable sheet does not melt, and a stretchable sheet having partially weakened stretchability can be continuously processed.

In the wearable article production method, it is preferable that the weakened region is formed at least at a part of the attachment location by forming a plurality of notches in the stretchable sheet in the weakening step.

In the production method, it is possible to easily and reliably weaken the stretchability of the elastic film and to form a weakened region in a predetermined range at least at a part of the attachment location in the stretchable sheet by forming a plurality of notches in the stretchable sheet.

In the wearable article production method, it is preferable that the notches are formed at least at a part of the attachment location using a cutter roll having a cutter provided on a peripheral surface of a roll main body while continuously transporting the stretchable sheet in the weakening step.

In the production method, it is possible to continuously form notches at the attachment location in the stretchable sheet that is continuously transported by using the cutter roll, and the processing efficiency in the weakening step is improved.

In the wearable article production method, it is preferable that the notches are formed in a state in which the cutter is heated to a temperature higher than a melting point of the elastic film in the weakening step.

In the production method, it is possible to more easily form notches in the elastic film by forming the notches in a state in which the cutter is heated to a temperature higher than the melting point of the elastic film.

In the wearable article production method, it is preferable that the weakened region is formed at least at a part of the attachment location by additionally performing ultrasonic welding on the stretchable sheet to form an additional joint in the weakening step.

In the production method, it is possible to locally increase the number of joints and to form the weakened region at least at a part of the attachment location by additionally performing ultrasonic welding on the stretchable sheet to form additional joints as a weakening step after the welding step. In this production method as well, ultrasonic welding is not simultaneously and mainly performed in the range of a part in the welding step when the stretchable sheet is formed and the temperature of the anvil roll or the ultrasonic horn does not rise as in the conventional case. As a result, the portion other than the joints in the stretchable sheet does not melt, and a stretchable sheet having partially weakened stretchability can be continuously processed. Moreover, in this weakening step, it is possible to form additional joints in an arbitrary number and arbitrary arrangement by additional ultrasonic welding, and thus the degree of freedom in the formation of weakened region is high.

In the wearable article production method, it is preferable that the weakened region is formed at a portion of at least a part of the attachment location by bringing the portion into contact with a heated member to perform a heat-sealing of the pair of sheet bodies and the elastic film with each other in the weakening step.

In the production method, a weakened region is formed at least at a part of the attachment location by heat-sealing a pair of sheet bodies and an elastic film with each other as a weakening step after the welding step, and thus ultrasonic welding is not mainly performed in the range of a part when the stretchable sheet is formed and the temperature of the anvil roll or the ultrasonic horn does not rise as in the conventional case. As a result, the portion other than the joints in the stretchable sheet does not melt, and a stretchable sheet having partially weakened stretchability can be continuously processed. Moreover, in this weakening step, the weakened region is formed by heat-sealing the pair of sheet bodies and the elastic film with each other, and it is thus possible to arbitrarily change the state of bonding between the pair of sheet bodies and the elastic film by changing the temperature for heat sealing. By setting the heat-sealed region as appropriate, it is possible to form a desired pattern (for example, a desired character or pattern) in the weakened region, and the design is improved.

In the wearable article production method, it is preferable that heat embossing is performed to form a predetermined shape by partially pressing the stretchable sheet in the thickness direction of the stretchable sheet while heating the stretchable sheet as the heat sealing.

In the production method, it is possible to reliably bond the pair of sheet bodies and the elastic film to each other by performing heat embossing to form a predetermined shape by partially pressing the stretchable sheet in the thickness direction of the stretchable sheet while heating the stretchable sheet as heat sealing. Moreover, it is possible to realize a three-dimensional effect by imparting irregularity to the weakened region in a desired pattern, and the visibility is improved while the design is further improved.

The wearable article production method preferably further includes a vent hole forming step of forming a vent hole in the elastic film after the welding step.

In the production method, it is possible to impart breathability to the elastic film by forming vent holes in the elastic film.

The wearable article according to an aspect of the present embodiments includes a stretchable sheet having stretchability; and an absorbent main body configured to absorb water, in which the absorbent main body is attached to a predetermined attachment location in the stretchable sheet, the stretchable sheet includes an elastic film having stretchability in a predetermined stretching direction and a pair of sheet bodies, the elastic film and the pair of sheet bodies are ultrasonically welded to each other at a plurality of joints by the plurality of joints separated from each other in the stretching direction in a state in which the elastic film in an elongated state is sandwiched between the pair of sheet bodies, a weakened region, where stretchability of the elastic film is weakened, is formed at least at a part of the attachment location in the stretchable sheet by a plurality of notches, and the absorbent main body is attached to the attachment location so as to overlap the weakened region.

In this configuration, the stretchable sheet includes an elastic film having stretchability and a pair of sheet bodies, and the elastic film and the pair of sheet bodies are ultrasonically welded to each other at the plurality of joints in a state in which the elastic film in an elongated state is sandwiched between the pair of sheet bodies. The weakened region where the stretchability of the elastic film is weakened is formed at least at a part of the attachment location, to which the absorbent main body is attached, in the stretchable sheet by the plurality of notches formed in the elastic film. By this, ultrasonic welding is not mainly performed in the range of a part when the stretchable sheet is formed and the temperature of the anvil roll or the ultrasonic horn does not rise as in the conventional case. As a result, the portion other than the joints in the stretchable sheet does not melt, and a stretchable sheet having partially weakened stretchability can be continuously processed. Moreover, the weakened region is formed by the notches, and it is thus possible to easily and reliably weaken the stretchability of the elastic film and to form the weakened region in a predetermined range.

The wearable article according to another aspect of the present embodiments includes a stretchable sheet having stretchability; and an absorbent main body configured to absorb water, in which the absorbent main body is attached to a predetermined attachment location in the stretchable sheet, the stretchable sheet includes an elastic film having stretchability in a predetermined stretching direction and a pair of sheet bodies, the elastic film and the pair of sheet bodies are ultrasonically welded to each other at a plurality of joints by the plurality of joints separated from each other in the stretching direction in a state in which the elastic film in an elongated state is sandwiched between the pair of sheet bodies, a weakened region, where stretchability of the elastic film is weakened, is formed at least at a part of the attachment location in the stretchable sheet by a portion at which the pair of sheet bodies and the elastic film are heat-sealed with each other, and the absorbent main body is attached to the attachment location so as to overlap the weakened region.

In this configuration, the stretchable sheet includes an elastic film having stretchability and a pair of sheet bodies, and the elastic film and the pair of sheet bodies are ultrasonically welded to each other at the plurality of joints in a state in which the elastic film in an elongated state is sandwiched between the pair of sheet bodies. The weakened region where the stretchability of the elastic film is weakened is formed at least at a part of the attachment location, to which the absorbent main body is attached, in the stretchable sheet by the portion at which the pair of sheet bodies and the elastic film are heat-sealed with each other. By this, ultrasonic welding is not mainly performed in the range of a part when the stretchable sheet is formed and the temperature of the anvil roll or the ultrasonic horn does not rise as in the conventional case. As a result, the portion other than the joints in the stretchable sheet does not melt, and a stretchable sheet having partially weakened stretchability can be continuously processed. Moreover, the weakened region is formed by heat-sealing the pair of sheet bodies and the elastic film with each other, and it is thus possible to arbitrarily change the state of bonding by changing the temperature for heat sealing. By setting the heat-sealed region as appropriate, it is possible to form a desired pattern (for example, a desired character or pattern) in the weakened region, and the design is improved.

In the wearable article, it is preferable that the stretchable sheet is partially pressed in a thickness direction of the stretchable sheet at the heat-sealed portion to form a predetermined shape.

In this configuration, the stretchable sheet is partially pressed in the thickness direction of the stretchable sheet at the portion heat-sealed by heat embossing or the like to form a predetermined shape, and it is thus possible to reliably bond the pair of sheet bodies and the elastic film in the stretchable sheet to each other. Moreover, it is possible to impart irregularity to the weakened region in a desired pattern, and the visibility is improved while the design is further improved.

The wearable article production device of the present embodiments is a production device of a wearable article including a stretchable sheet having stretchability and an absorbent main body that is attached to a predetermined attachment location in the stretchable sheet and is configured to absorb water, the production device including a welding unit for ultrasonically welding a pair of sheet bodies and an elastic film to each other at a plurality of joints separated from each other in a predetermined transport direction in a region including the attachment location by transporting a sheet laminate formed by sandwiching the elastic film in an elongated state between the pair of sheet bodies in the transport direction so that the sheet laminate passes between an anvil roll and an ultrasonic horn to form the stretchable sheet; a weakening unit that is arranged on a downstream side of the welding unit in the transport direction and is for forming a weakened region, where stretchability of the elastic film is weakened, at least at a part of the attachment location in the stretchable sheet; and an attachment unit that is arranged on a downstream side of the welding unit in the transport direction and is for attaching the absorbent main body to the attachment location so that the absorbent main body overlaps the weakened region.

In the production device, it is possible to form a stretchable sheet by ultrasonic welding in the region including the attachment location in the welding unit, and then weaken the stretchability of the elastic film at least at a part of the attachment location for the absorbent main body in the stretchable sheet in the weakening unit arranged on the downstream side of the welding unit in the transport direction. By this, ultrasonic welding is not mainly performed in the range of a part in order to form the weakened region when the stretchable sheet is formed and the temperature of the anvil roll or the ultrasonic horn does not rise as in the conventional case. As a result, the portion other than the joints in the stretchable sheet does not melt, and a stretchable sheet having partially weakened stretchability can be continuously processed.

As described above, according to the wearable article production method, the wearable article, and the wearable article production device of the present embodiments, it is possible to continuously process a stretchable sheet having partially weakened stretchability.

The invention claimed is:

1. A production method of a wearable article including a stretchable sheet having stretchability, an absorbent main body that is attached to a predetermined attachment location in the stretchable sheet and is configured to absorb water, a front part, and a back part, the production method comprising:

ultrasonically welding a pair of sheet bodies and an elastic film to each other at a plurality of joints separated from each other in a predetermined transport direction in a region of a front abdomen constituting the front part and a back abdomen constituting the back part including the attachment location by transporting a sheet laminate formed by sandwiching the elastic film in an elongated state between the pair of sheet bodies in the transport direction so that the sheet laminate passes between an anvil roll and an ultrasonic horn to form the stretchable sheet, the plurality of joints being uniformly formed throughout an entirety of the region of the front abdomen and the back abdomen of the stretchable sheet;

applying a weakening treatment to a specified portion of the stretchable sheet to form a weakened region in the attachment location after the ultrasonic welding, the weakened region having a smaller stretchability than another portion of the stretchable sheet to which no weakening treatment has been applied; and attaching the absorbent main body to the attachment location so that the absorbent main body overlaps the weakened region, wherein the applying of the weakening treatment includes forming the weakened region at least at a part of the attachment location by forming a plurality of notches so as to be separated from each other in the transport direction and an orthogonal direction that is orthogonal to the transport direction in the stretchable sheet, a length of each notch in the orthogonal direction being larger than a diameter of each joint in the orthogonal direction.

2. The wearable article production method according to claim 1, wherein the notches are formed at least at a part of the attachment location using a cutter roll having a cutter provided on a peripheral surface of a roll main body while continuously transporting the stretchable sheet in the applying of the weakening treatment.

3. The wearable article production method according to claim 2, wherein the notches are formed in a state in which the cutter is heated to a temperature higher than a melting point of the elastic film in the applying of the weakening treatment.

4. The wearable article production method according to claim 1, further comprising forming a vent hole in the elastic film after the ultrasonic welding.

5. The wearable article production method according to claim 2, further comprising forming a vent hole in the elastic film after the ultrasonic welding.

6. The wearable article production method according to claim 3, further comprising forming a vent hole in the elastic film after the ultrasonic welding.

\* \* \* \* \*